United States Patent
Ise et al.

(10) Patent No.: US 6,768,542 B2
(45) Date of Patent: Jul. 27, 2004

(54) DEFECT INSPECTING DEVICE FOR SUBSTRATE TO BE PROCESSED AND METHOD OF MANUFACTURING SEMICONDUCTOR DEVICE

(75) Inventors: Hirotoshi Ise, Tokyo (JP); Toshiki Oono, Tokyo (JP); Yasuhiro Kimura, Tokyo (JP); Toshio Komemura, Tokyo (JP); Masato Toyota, Tokyo (JP); Toshihiko Noguchi, Tokyo (JP)

(73) Assignees: Renesas Technology Corp., Tokyo (JP); Mitsubishi Electric Engineering Company Limited, Tokyo (JP)

( * ) Notice: Subject to any disclaimer, the term of this patent is extended or adjusted under 35 U.S.C. 154(b) by 29 days.

(21) Appl. No.: 10/219,292

(22) Filed: Aug. 16, 2002

(65) Prior Publication Data

US 2003/0053046 A1 Mar. 20, 2003

(30) Foreign Application Priority Data

Sep. 19, 2001 (JP) ......................................... 2001-285527

(51) Int. Cl.⁷ .............................................. G01N 21/00
(52) U.S. Cl. ................................. 356/237.2; 356/237.1
(58) Field of Search ........................... 356/237.1–237.6, 356/394; 250/559.41, 559.48, 559.22, 559.45

(56) References Cited

U.S. PATENT DOCUMENTS

| | | | | |
|---|---|---|---|---|
| 4,342,515 A | * | 8/1982 | Akiba et al. .............. 356/237.3 |
| 4,505,585 A | * | 3/1985 | Yoshikawa et al. ....... 356/237.2 |
| 5,194,743 A | * | 3/1993 | Aoyama et al. ............. 250/548 |
| 5,471,066 A | * | 11/1995 | Hagiwara ............... 250/559.18 |
| 5,602,401 A | * | 2/1997 | Broude et al. .......... 250/559.45 |
| 5,995,218 A | * | 11/1999 | Ide ........................... 356/237.1 |
| 6,222,624 B1 | * | 4/2001 | Yonezawa ................ 356/237.1 |

FOREIGN PATENT DOCUMENTS

| | | |
|---|---|---|
| JP | 5-160245 | 6/1993 |
| JP | 8-264606 | 10/1996 |
| JP | 9-186209 | 7/1997 |
| JP | 11-326229 | 11/1999 |

* cited by examiner

*Primary Examiner*—Frank G. Font
*Assistant Examiner*—Sang H. Nguyen
(74) *Attorney, Agent, or Firm*—McDermott Will & Emery LLP (57) ABSTRACT

A defect inspecting device for a wafer is built in a positioning device for positioning a wafer 1, as a substrate to be processed, in a semiconductor manufacturing process. Light is irradiated on the wafer held on a vacuum holding base 2 while rotating the wafer at least one rotation from a position where the wafer is positioned and the scattered light is received. An operation unit 14 and a control unit 15 judge that if the intensity of the scattered light exceeds a predetermined threshold, a defect is detected on the wafer 1.

11 Claims, 6 Drawing Sheets

| ID | Key_No. | Vend | Line | Angle | Level | OF | mm | Photo_Name | TIME |
|---|---|---|---|---|---|---|---|---|---|
| 1 | ASB3300 | A COMPANY | AS | 170.5 | 2000 | | | 2slit-1PHOTO | 19980101 |
| 2 | AT15600 | A COMPANY | AS | 190.9 | 2000 | | | 2slit-2PHOTO | 19980101 |
| 3 | AT15600 | A COMPANY | AS | 282.9 | 2000 | | | 2slit-3PHOTO | 19980101 |
| 6 | AT15600 | A COMPANY | AS | | 1866 | 1 | 2 | 2slit-4PHOTO | 19980101 |
| 7 | AT15600 | A COMPANY | AS | 191.8 | 2000 | | | 3slit-1PHOTO | 19980101 |
| 8 | AT15600 | A COMPANY | AS | 171.3 | 2000 | | | 3slit-2PHOTO | 19980101 |
| 9 | AT15600 | A COMPANY | AS | 187.9 | 1636 | | | 4slit-1PHOTO | 19980101 |
| 10 | AT15600 | A COMPANY | AS | 191.9 | 1540 | | | 4slit-2PHOTO | 19980101 |
| 11 | AT15600 | A COMPANY | AS | 171.9 | 1297 | | | 5slit-1PHOTO | 19980101 |
| 12 | AT15600 | A COMPANY | AS | 192.4 | 2000 | | | 5slit-2PHOTO | 19980101 |

DEFECT INSPECTING DEVICE FOR SUBSTRATE TO BE PROCESSED AND METHOD OF MANUFACTURING SEMICONDUCTOR DEVICE

BACKGROUND OF THE INVENTION

1. Field of the Invention

The present invention relates to a defect inspecting device for a substrate to be processed in a semiconductor manufacturing process, and in particular, to a device used in a positioning device for a substrate and a method of manufacturing a semiconductor device.

2. Description of the Related Art

In general, a semiconductor manufacturing process includes a plurality of processes and processes a wafer as a substrate to be processed by the plurality of processes to manufacture a semiconductor device (H semiconductor chip). In this semiconductor manufacturing process, it is necessary to preclude the misalignment of the wafer so as to prevent or suppress a defect occurred in the course of processing and transfer. For this reason, there has been used a positioning device for positioning the wafer with high accuracy.

Figure 8:
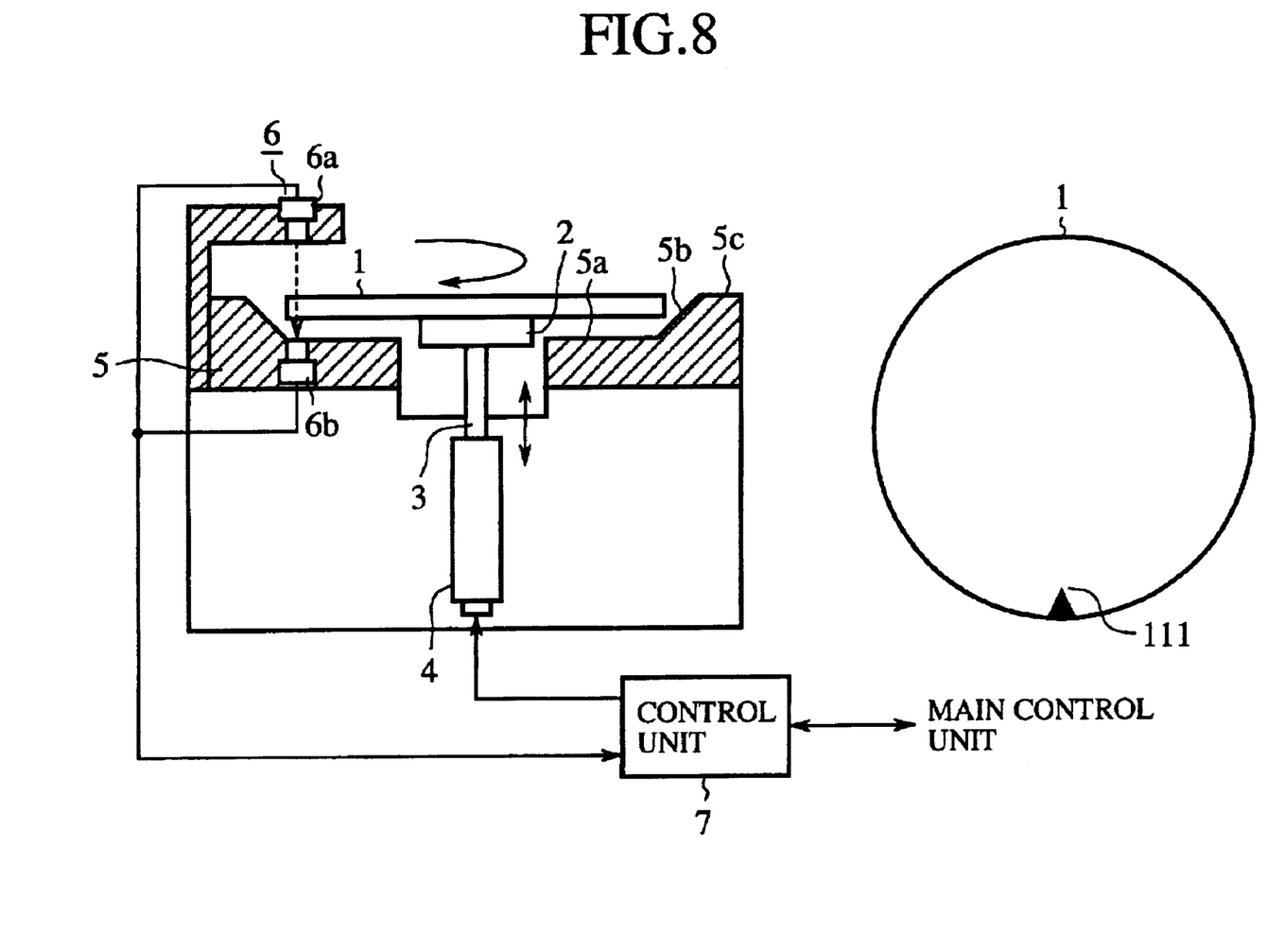
FIG. 8 is a block diagram showing a conventional positioning device for a substrate to be processed.

FIG. 8 is a block diagram showing a conventional positioning device.

Referring to FIG. 8, a reference numeral 1 denotes a wafer as a substrate to be processed; a reference numeral 2 a vacuum holding base; a reference numeral 3 a cylinder; a reference numeral 4 an actuator; a reference numeral 5 an alignment member; a reference numeral 6 a transmission sensor; and a reference numeral 7 a control unit. The alignment member 5 is provided with the first flat plane 5a with the first radius, a slope 5b inclined upward at a predetermined angle from the peripheral of the first flat plane 5a, and a second flat plane 5c extending outward in the radial direction of the top end of the slop 5b and with the second radius. The first radius is equal to the second ones. The control unit 7 drives and controls the actuator 4 and the transmission sensor 6 in response to a control signal given by the control unit of a semiconductor production equipment (hereinafter referred to as a main control unit (not shown)). Then, the cylinder 3 is driven in the vertical direction within a range (moving range) predetermined by the actuator 4. Further, the cylinder 3 is rotated by the actuator 4. Thereby, the vacuum holding base 2 is moved in the vertical direction within a range predetermined by the first flat plane 5a and the second flat plane 5c and, at the same time, is rotated by taking the cylinder 3 as the axis of rotation. The wafer 1 is formed in a circle, for example, and a notch 111 is previously formed on the rim of the wafer 1. The notch 111 is devoted to positional detection.

Next, the operation of the conventional positioning device will be described.

The semiconductor production equipment (not shown) is provided with a carrier robot (not shown) and the wafer 1 is transferred by the carrier robot to the vacuum holding base 2 and is placed on the vacuum holding base 2, with its main plane (top surface) abutted against the vacuum holding base 2. In the case where the wafer 1 is placed on the vacuum holding base 2, when the cylinder 3 is moved to the uppermost position within the moving range, that is, when the vacuum holding base 2 is positioned at the uppermost position, the wafer 1 is placed on the vacuum holding base 2 by the carrier robot. At this time, the surface of the wafer 1 is a little lower than the second flat plane 5c.

After the wafer 1 is placed on the vacuum holding base 2 in this manner, the cylinder 3 is moved in the vertical direction in FIG. 8 by the actuator 4 and then the vacuum holding base 2, that is, the wafer 1 is lowered. When the vacuum holding base 2 is lowered, the rim of the wafer 1 is lowered along the slope 5b and the top surface of the vacuum holding base 2 reaches the first flat plane 5a, the rim of the wafer 1 is positioned at the peripheral of the first flat plane 5a; that is, the wafer is centered.

Then, the wafer 1 is vacuum absorbed by the vacuum holding base 2 and then the cylinder 3 is moved upward by the actuator 4 to move up the vacuum holding base 2, that is, the wafer 1. Thereafter, the cylinder 3 is rotated by the actuator 4 to rotate the vacuum holding base 2, that is, the wafer 1 in the direction shown by an arrow in FIG. 8 by taking the cylinder 3 as the axis of rotation.

The transmission sensor 6 has a light projecting part 6a and a light receiving part 6b and, as shown in FIG. 8, the light projecting part 6a is opposed to the light receiving part 6b across the peripheral of the wafer 1. The control unit 7 drives the light projecting part 6a to emit light. As described above, the wafer 1 has the notch 111, so that when the notch 111 reaches a position where the transmission sensor 6 is arranged, the light emitted from the light projecting part 6a passes through the notch 111 and is received by the light receiving part 6b. That is to say, the wafer 1 is rotated until the light emitted from the light projecting part 6a is received by the light receiving part 6b to adjust the angle of the wafer 1. In other words, the control unit 7 rotates the wafer 1 until the notch 111 is detected by the transmission sensor 6 to adjust the angle of the wafer 1 (position of the wafer 1).

The angle (position) of the wafer 1 is adjusted in this manner and then the wafer 1 is received by the carrier robot and is transferred to a processing unit (processing chamber) attached to the semiconductor production equipment.

In the processing and the transfer processes of the wafer 1, as described above, it is necessary to position the wafer 1 and to inspect a defect on the wafer 1 such as a foreign matter adhered thereto and a crack (chip at the end of the wafer 1). In Japanese Patent Unexamined Publication No. 9-186209 (hereinafter referred to as a first prior art 1), there is disclosed a device (inspection device) for inspecting a defect on a wafer. In the first prior art, a wafer positioning unit is provided with a macro-inspecting function and when the wafer is positioned by detecting a positioning notch formed on the rim of the wafer, the wafer is slanted and vibrated to perform a macro observation. Further, in Japanese Patent Unexamined Publication No. 11-326229, there is disclosed a device in which a defect on a wafer is inspected when the wafer is positioned on an inspection stage with high accuracy (hereinafter referred to as a second prior art). That is to say, in the second prior art, a laser beam is irradiated on the inspection region (foreign matter detecting region) on the wafer and the upper scattered light is received by a detection optical system provided above in the vertical direction of an inspection table to detect a foreign matter. At this time, the coordinates of the center of the wafer are calculated and the calculated coordinates of the center are taken as the coordinates of the center of the wafer when the foreign matter is detected.

Further, in Japanese Patent Unexamined Publication No. 5-160245 (hereinafter referred to as a third prior art), there is disclosed a device for positioning a wafer and detecting a defect on the rim of the wafer. In the third prior art, the device includes a first rotary stage slightly rotatable nearly around the origin of an orthogonal coordinate system, a direct-moving stage mounted on the first rotary stage and two-dimensionally movable in the orthogonal coordinate system, and a second rotary stage mounted on the direct-moving stage and rotatable one rotation or more while holding the wafer. While the second rotary stage is rotating, the defect (chip or the like) on the rim of the wafer is detected by output information from the first detector for detecting information indicative of the change of displacement of the rim of the wafer from the center of rotation on a non-contact base.

In addition, in Japanese Patent Unexamined Publication No. 8-264606 (hereinafter referred to as a fourth prior art), there is disclosed a device for positioning a wafer on an X-Y stage in inspecting a foreign matter on the wafer. In the fourth prior art, the alignment of the wafer is checked by an observation-alignment optical system. Further, a foreign matter detected by the observation-alignment optical system is visually checked and depending on the observation results of the shape of the detected foreign matter, the pass or fail of the wafer is determined.

The conventional defect inspecting device for a substrate to be processed is constituted in the above manner. Even though, in any one of the prior arts 1 to 4, the wafer is inspected when positioning the wader, only the existence of the foreign matter is detected visually or by the detection optical system. Hence, it is impossible to inspect a defect such as a foreign matter or a chip on the wafer as to what shape it has or where it is. In order to make such an inspection, it has to inspect the wafers on which the existence of the defect is identified one by one in detail, for example, under a microscope.

In this manner, the conventional defect inspecting device for a substrate to be processed involves a problem that it is difficult to detect a defect on the wafer with high accuracy in positioning the wafer.

SUMMARY OF THE INVENTION

The present invention has been made to solve the above problems. It is an object of the present invention to provide a defect inspecting device for a substrate to be processed, capable of detecting a defect on a wafer, as a substrate to be processed, with high accuracy in positioning the wafer, and a method for inspecting a defect on a substrate to be processed.

It is another object of the present invention to provide a defect inspecting device for a substrate to be processed, capable of eliminating the need for inspecting a defect on a wafer visually or microscopically or the like and easily detecting the abnormality of the wafer, and a method for inspecting a defect on a substrate to be processed.

It is still another object of the present invention to provide a semiconductor device capable of improving productivity of a semiconductor device by the above-mentioned device for inspecting a defect on a substrate to be processed.

A defect inspecting device for a substrate to be processed according to the present invention is built in a positioning device for positioning a substrate in a semiconductor manufacturing process and includes an inspection unit for inspecting a defect on the substrate, after the substrate is positioned, while rotating the substrate at least one rotation from a position where the substrate is positioned, and an angle information calculating means for finding a defective position, when a defect is detected on the substrate, as angle information indicative of the angle of rotation of the substrate.

A method for manufacturing a semiconductor device having a defect inspecting device for a substrate to be processed according to the present invention is built in a positioning device for positioning the substrate in a semiconductor manufacturing process and includes inspecting means for inspecting a defect on the substrate, after the substrate is positioned, while rotating the substrate at least one rotation from the position where the substrate is positioned, the method including the step of removing the substrate from a semiconductor manufacturing process when the inspection means judges the substrate to be defective.

A method for manufacturing a semiconductor device having a defect inspecting device for a substrate to be processed according to the present invention is built in a positioning device for positioning the substrate in a semiconductor manufacturing process and includes inspecting means for inspecting a defect on the substrate, after the substrate is positioned, while rotating the substrate at least one rotation from a position where the substrate is positioned, said inspecting means including judging means for judging that a defect is detected on the substrate when the intensity of the scattered light exceeds a predetermined threshold and sending an alarm signal, the method including the step of raising an alarm upon reception of an alarm signal to temporarily stop a semiconductor manufacturing process

DESCRIPTION OF THE PREFERRED EMBODIMENTS

The preferred embodiments of the present invention will hereinafter be described in detail with reference to the accompanying drawings.

First Embodiment

Figure 1:
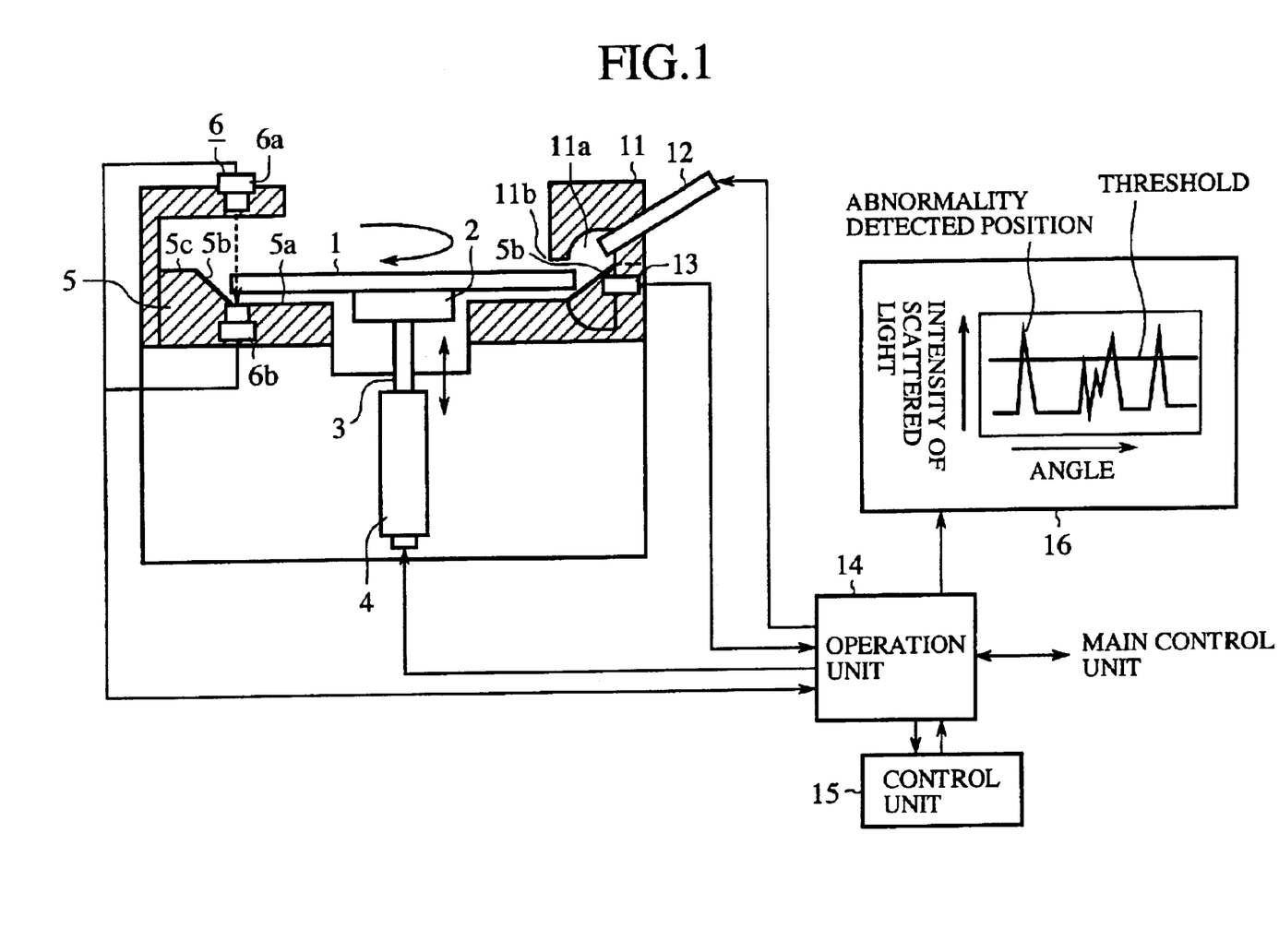
FIG. 1 is a block diagram showing a defect inspecting device for a substrate to be processed according to a first embodiment of the present invention.

In FIG. 1, like reference numerals as in FIG. 8 designate like components. In the first embodiment shown in FIG. 1, on the peripheral of an aligning member 5, a defect inspecting block 11 is integrally formed on a part thereof with the alignment member 5. In this defect inspecting block 11 a hollow 11a is formed into which the rim of a wafer 1 is inserted. In this hollow 11a, the open end 11b into which the wafer 1 is inserted has the same width as a distance between the first flat plane 5a and the second flat plane 5c. That is, a lower wall (bottom end) defining the open end 11b is at the same level as the first flat plane 5a and an upper wall (top end) defining the open end 11b is at the same level as the second flat plane 5c. As a result, when the wafer 1 is placed on a vacuum holding base 2 by a carrier robot, the rim of the wafer 1 is inserted into the hollow 11a from the rear or the front of a paper of FIG. 1 to place the wafer 1 on the vacuum holding base 2.

Referring to FIG. 1, a reference numeral 12 denotes a light source; a reference numeral 13 a scattered light receiving part; a reference numeral 14 an operation unit; a reference numeral 15 a control unit; and a reference numeral 16 a monitor. The operation unit 14 is connected to a transmission sensor 6 (light projecting part 6a and light receiving part 6b), an actuator 4, the light source 12, the scattered light receiving part 13, the control unit 15, the monitor 16, and the control unit of a semiconductor production equipment (hereinafter referred to as a main control unit). The operation unit 14 positions the wafer 1 cooperated with the control unit 15 and inspects a defect, as will be described later. The light source 12 is mounted on the defect inspecting block 11 and is faced toward the inside of the hollow 11a. When the wafer 1 is held by the vacuum holding base 2, light from the light source 12 is irradiated on the rim of the wafer 1. On the other hand, as shown in FIG. 1, the scattered light receiving part 13 is mounted on the defect inspecting block 11 at a position opposed to the peripheral surface of the wafer 1, with the wafer 1 positioned.

Next, the operation of the defect inspecting device of the first embodiment will be described.

As shown in FIG. 8, after the wafer 1 having a notch 111 is positioned, the notch 111 is detected and then the angle (position) of the wafer 1 is adjusted. At this time, the operation unit 14 controls the actuator 4 and the transmission sensor 6 in response to a control signal sent by the main control unit.

As described above, after the positioning of the wafer 1 is completed, that is, after the angle of the wafer 1 is adjusted, the operation unit 14 drives the light source 12 to irradiate, for example, a laser beam on the rim of the wafer 1. When this laser beam is irradiated on the rim of the wafer 1, it is diffraction scattered thereon. The diffraction scattered light is received by the scattered light receiving part 13 and is given to the operation unit 14 as a detected signal. Then, the operation unit 14 inspects a defect on the wafer 1 in response to the detected signal (that is, diffraction scattered light).

Figure 2:
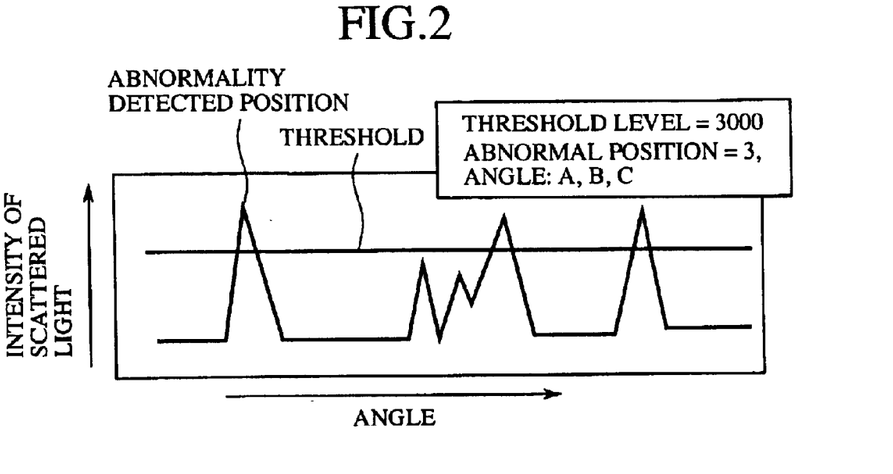
FIG. 2 is a chart showing an example of an anomalous detection result displayed on the monitor shown in FIG. 1.

In inspecting a defect on the wafer 1, as described above, the wafer 1 is positioned and then the wafer 1 is rotated at least one rotation by taking a cylinder 3 as the axis of rotation (as described above, the position of the positioned wafer (positioned position) is held in the operation unit 14, so the operation unit 14 rotates the wafer 1 one rotation based on the positioned position). For example, the operation unit 14 rotates the wafer 1 one rotation at each sampling unit set by the control unit 15. This sampling unit is, for example, 0.1 degree and, as described above, the operation unit 14 receives the diffraction scattered light every time the wafer 1 is rotated by 0.1 degree. The control unit 15 sets the intensity of previously predetermined anomalous detection scattered light, as a threshold in the operation unit 14. The operation unit 14, as shown in FIG. 2, displays the threshold and the intensity of the detected signal (intensity of the detected scattered light) on the monitor 16 depending on the sampling unit (the angle of rotation). In the example shown in FIG. 2, the threshold level is 3000 and the detected scattered light is displayed on the monitor 16 depending on the angle of rotation of the wafer 1. That is to say, the intensity of detected scattered light is continuously displayed, with the intensity of scattered light as a vertical axis and an angle (angle of rotation) as a horizontal axis, on the monitor 16 together with the threshold. This makes it possible for the operator to see the intensity of detected scattered light over the threshold at a glance. The intensity of the detected scattered light over the threshold indicates the anomalous detection and the horizontal axis corresponding to the position where the abnormality is detected indicates the angle information of the wafer 1 (in FIG. 2, there are three positions where abnormality is detected and their angle information are A, B, and C. A wafer angle corresponding to the position where the abnormality is detected is hereinafter referred to as an anomalous wafer detection angle).

Further, the operation unit 14 compares the detected scattered light with the threshold every sampling unit to inspect the presence or absence of a defect on the wafer 1. The rate at which the laser beam irradiated from the light source 12 is diffraction scattered on the wafer 1 depends on the defect on the wafer 1 such as a flaw. That is to say, the larger the defect on the wafer 1 is, the larger the rate at which the laser beam is scattered is. For this reason, the maximum intensity of scattered light is previously measured, which corresponds to the largest defect on the wafer 1 negligible as a product. Assuming that this maximum intensity of scattered light is set as a threshold, as described above, the operation unit 14 compares the intensity of detected scattered light obtained at each 0.1 degree with the threshold. Then, if the intensity of the detected scattered light exceeds the threshold, the operation unit 14 identifies that a defect is detected on the wafer 1 at the position of the angle of rotation. Then, when the operation unit 14 identifies that a defect is detected on the wafer 1, it sends an anomalous detection signal to the control unit 15. Thereby, the control unit 15 is informed that a defect is detected on the wafer 1, stops the processing of the wafer 1, and gives an operator an alarm. Incidentally, the above mentioned anomalous detection signal may be given to the main control unit to stop the processing of the wafer 1.

As can easily be understood from the above description, the operation unit 14, the control unit 15, the light source 12, the scattered light receiving part 13, the actuator 4, the cylinder 3 and the vacuum holding base 2 function as inspecting means and the operation unit 14 and the control unit 15 function as angle information calculating means.

As described above, according to the first embodiment, the threshold is displayed on the monitor 16 and the intensity of detected scattered light is displayed depending on the angle information of the wafer 1, so that it is possible for the operator to see the intensity of detected scattered light over the threshold at a glance, and to find the angle information of the wafer 1 corresponding to the intensity of detected scattered light over the threshold. In other words, the operator can see where the defect such as a flaw is at the angle information at a glance. As a result, the operator can easily judge whether or not the abnormality is on the wafer 1.

Further, when a defect such as a flaw is detected on the wafer 1, if the processing of the wafer 1 is stopped and an alarm is given to the operator, it enables a quick address to the defect on the wafer in producing a semiconductor device and avoids a probable trouble in the semiconductor production equipment before hand. As a result, this improves productivity of the semiconductor device.

Second Embodiment

In a defect inspecting device according to the second embodiment, when a wafer surface defect display command (wafer map display command) is given from an input device (not shown) connected to the control unit 15 to the control unit 15, the control unit 15 causes the operation unit 14 display a wafer map. At this time, the control unit 15 gives wafer periphery information indicative of the center and radius of the wafer 1 to the operation unit 14. As described above, the operation unit 14 detects the abnormality of the wafer depending on the angle information of the wafer and takes the information of the wafer angle at which the abnormality is detected as wafer anomalous detection angle information.

Figure 3:
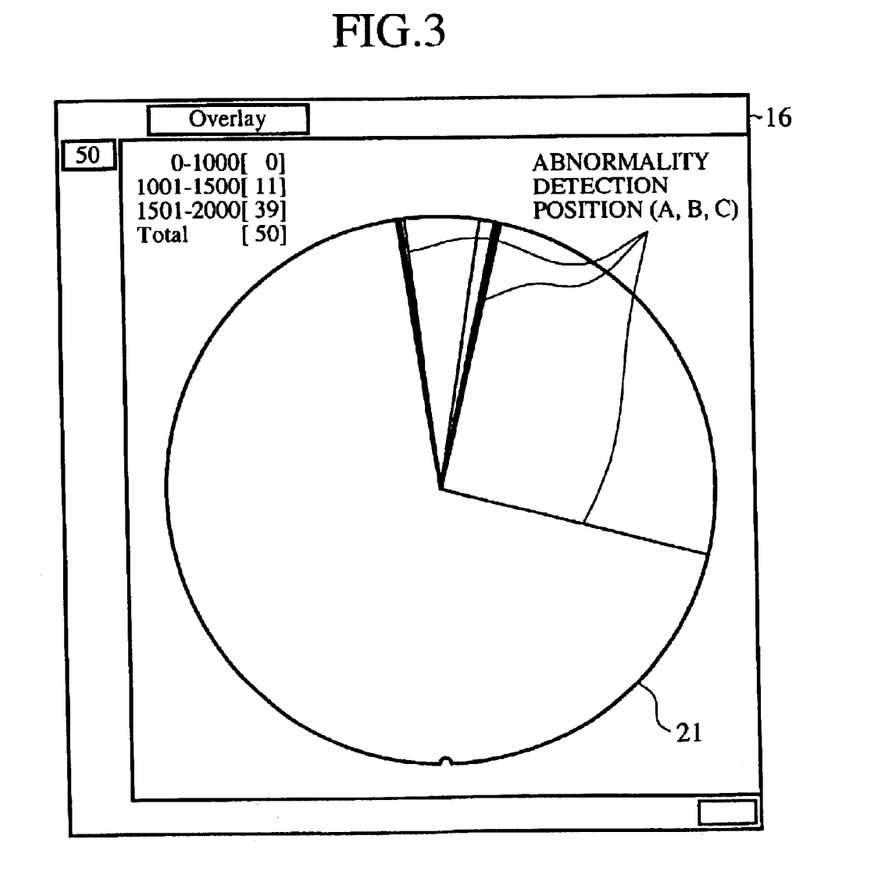
FIG. 3 is a graph showing defective positions on a wafer displayed on a monitor by a defect inspecting device for a substrate to be processed according to a second embodiment of the present invention.

Now, referring to a graph in FIG. 3, the operation unit 14 displays the contour of the wafer as a wafer pattern 21 on the monitor 16 based on the wafer periphery information and plots a defective position (where abnormality is detected) on the periphery of the wafer pattern 21 depending on the wafer abnormality detection angle information. In the second embodiment shown in FIG. 2, the wafer abnormality detection angle information are A, B, and C, so that the operation unit 14 plots the defective positions on the periphery of the wafer pattern 21 depending on the wafer anomalous detection angle information A, B, and C.

The operation unit 14 draws straight-line components, with the defective positions as start points and the center of the wafer 1 as an end point. Here, the length of each straight-line component represents the intensity of detected scattered light. In other words, if the intensity of detected scattered light is weak, the straight line component is short and if the intensity of detected scattered light is strong, the straight line component is long. That is, the length of the straight line component varies depending on how many the defects are. Further, the width of the straight-line component represents an angle range where the defect is over the threshold and represents to what extent the defective positions are extended on the wafer 1.

In this manner, the operation unit 14 displays a wafer map in which the defective position is displayed on the wafer pattern 21 by the straight-line component. At this time, the length of the straight-line component represents how many defects are and the width thereof represents how far the defects are expanding.

As described above, in the second embodiment, the wafer map is displayed on the monitor 16 to represent by the straight line component where the defective position such as a flaw is on the wafer pattern 21, how many defects are by the length thereof, and how far the defects are expanding by the width thereof. Therefore, it is possible to correctly identify not only the defective position on the wafer 1 but also how many defects are and how far the defects are expanding. As a result, it is possible to correctly and quickly identify the defective position (anomalous position) on the wafer 1.

Third Embodiment

In a defect inspecting device according to the third embodiment, in FIG. 1, every time a defect is inspected on the wafer, the operation unit 14 is given from a main control unit, for example, numbers (ID and Key number) relating to the wafer, vendor (Vend), production line (Line), and processing time (TIME) as wafer processing information. Further, the operation unit 14 produces wafer defect information by bringing anomalous detection angle information (Angle) and the intensity of detected scattered light at that time into correspondence with the wafer processing information and sends the wafer defect information to the control unit 15. The control unit 15 outputs the wafer defect information as a wafer defect information file to a storage device (not shown) and stores it.

Figure 4:
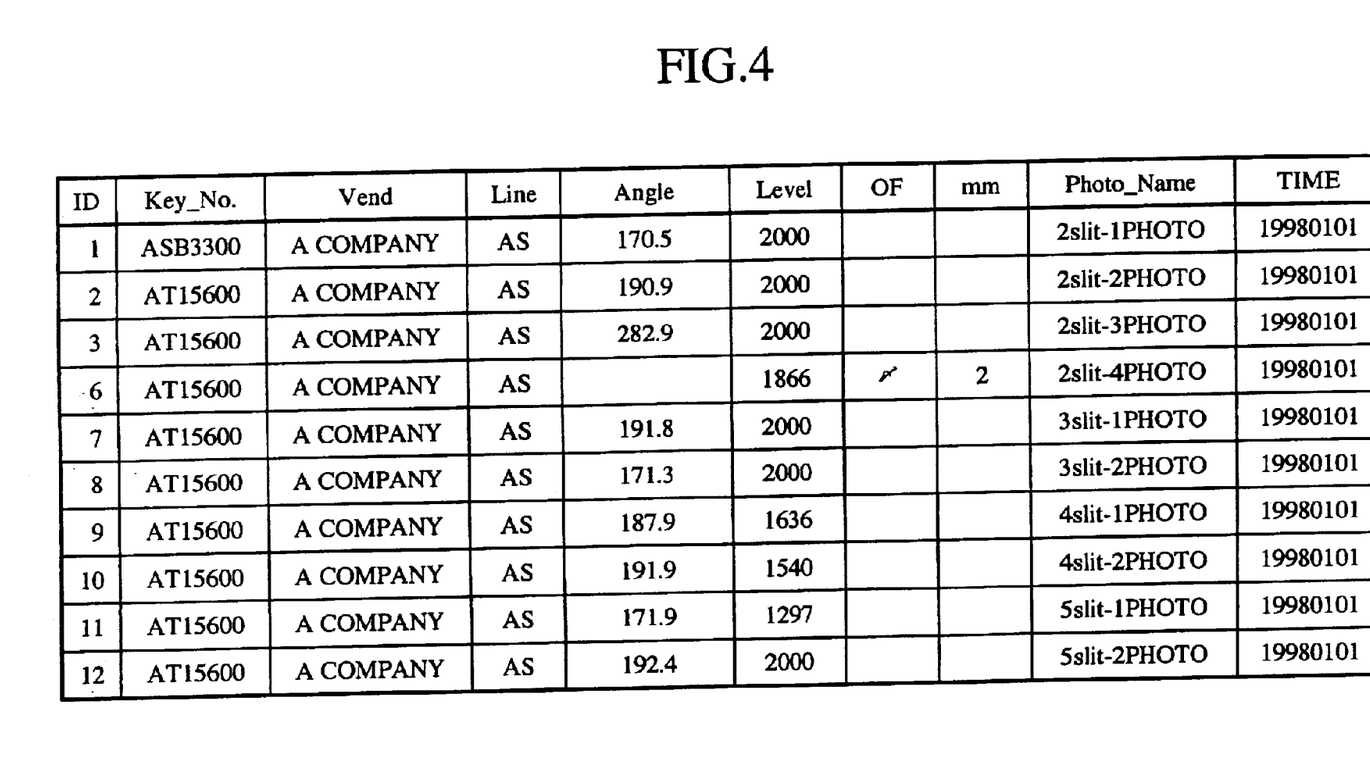
FIG. 4 is a table showing an example of an anomalous detection angle information file.

FIG. 4 is a table showing an example of the wafer defect information file stored in the storage device. In this wafer defect information file, the anomalous detection angle information (Angle) and the intensity of detected scattered light (Level) are stored in correspondence with ID, Key number, Vend and Line, and further the processing time (TIME) is added thereto.

The above wafer defect information file, as shown in FIG. 4, may be provided with a column for a photo-name (Photo-Name). The Photo-Name column is linked to the defect image for a defect such as a flaw and by specifying the Photo-Name column, the defect image corresponding to it is taken from the storage device and displayed, for example, on the monitor 16.

Figure 5:
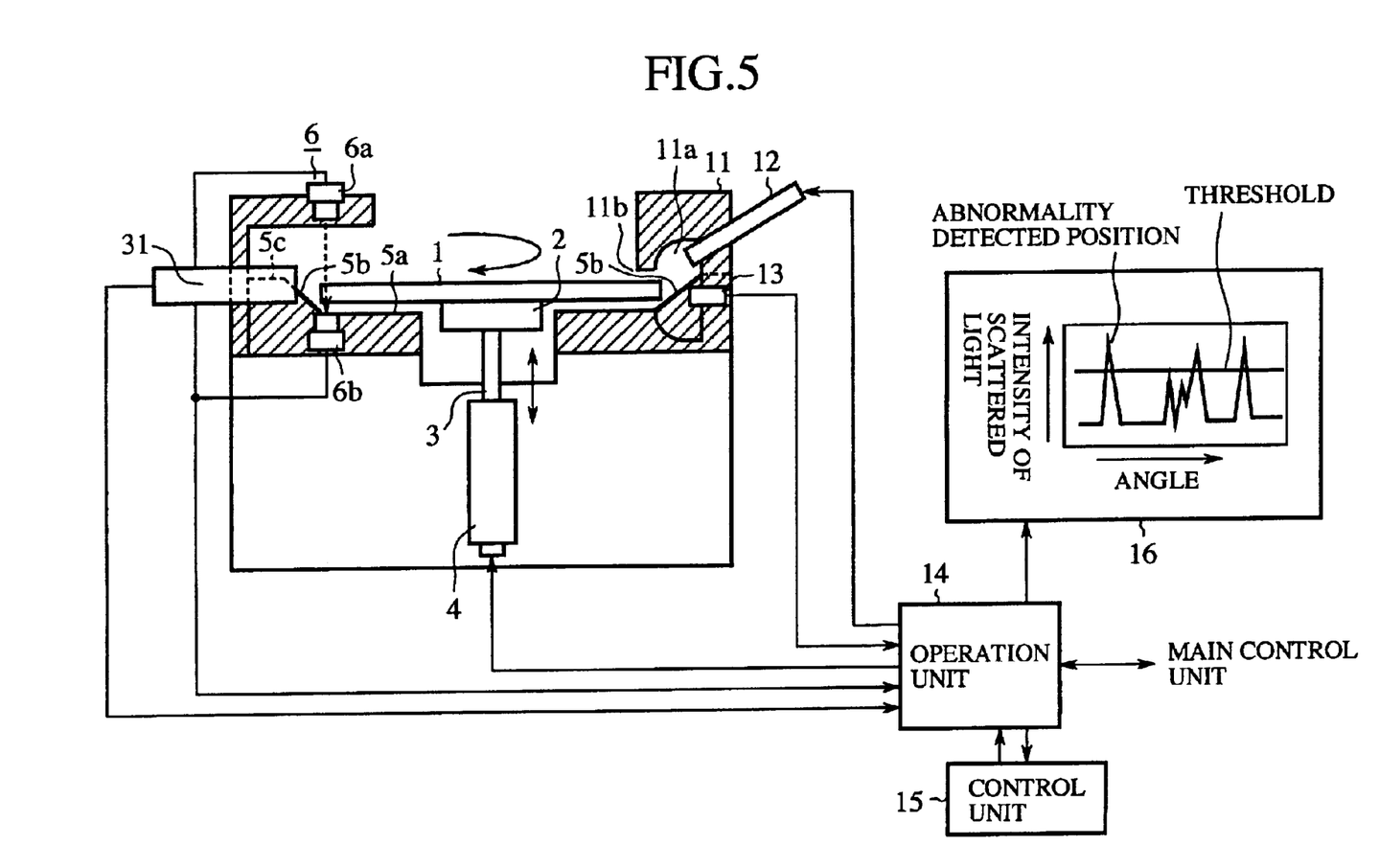
FIG. 5 is a block diagram showing a defect inspecting device for a substrate to be processed according to a third-embodiment of the present invention.

In order to take an image of the defect such as a flaw, for example, a defect inspecting device shown in FIG. 5 is used. In FIG. 5, like reference numerals as in FIG. 1 designate like components and descriptions thereof is omitted for brevity sake. As shown in FIG. 5, a photoelectric conversion device (for example, CCD camera: imaging means) 31 is disposed at a position opposed to a scattered light receiving part 13. In other words, in FIG. 5, the photoelectric conversion device 31 is arranged at a position separated 180 degree from the scattered light receiving part 13 (while the photoelectric conversion device 31 is arranged at the position separated 180 degree from the scattered light receiving part 13 in FIG. 5, it is not necessarily to arrange the photoelectric conversion device 31 at the position separated 180 degree from the scattered light receiving part 13 but it is essential only to find the relationship between the photoelectric conversion device 31 and the scattered light receiving part 13.)

Now, if a defect on the wafer 1 is inspected by a sampling unit of 0.1 degree, the operation unit 14 can obtain detected scattered light every time the wafer 1 is rotated 0.1 degree. Then, the operation unit 14 compares the detected scattered light with a threshold and if the compared result revealed to have a relationship (the intensity of detected scattered light ≧ the threshold), an angle corresponding to the intensity of detected scattered light is taken as anomalous detection angle information. The positional relationship between the scattered light receiving part 13 and the photoelectric conversion device 31 (180 degree in FIG. 5) is given to the operation unit 14 from the control unit 15 and when the wafer 1 is rotated from the anomalous detection angle information by an angle indicated by the positional relationship between the scattered light receiving part 13 and the photoelectric conversion device 31, an image given from the photoelectric conversion device 31 is taken as a wafer defect image corresponding to the anomalous detection angle information (see FIG. 6). The operation unit 14 gives the control unit 15 the anomalous detection angle information and a wafer defect image in pairs.

The control unit 15 adds a photo-name to the wafer defect image and stores the photo-name in a column of Photo-Name in correspondence with an ID, a Key number, a Vend, a Line and anomalous detection angle information (Angle) and the wafer defect image (with the photo-name) as an image file in a storage device. If the wafer defect image is stored in this manner, only by specifying the Photo-Name, the wafer defect image corresponding to the ID, the Key number, the Vend, the Line and the anomalous detection angle information (Angle) can be perused.

Figure 6:
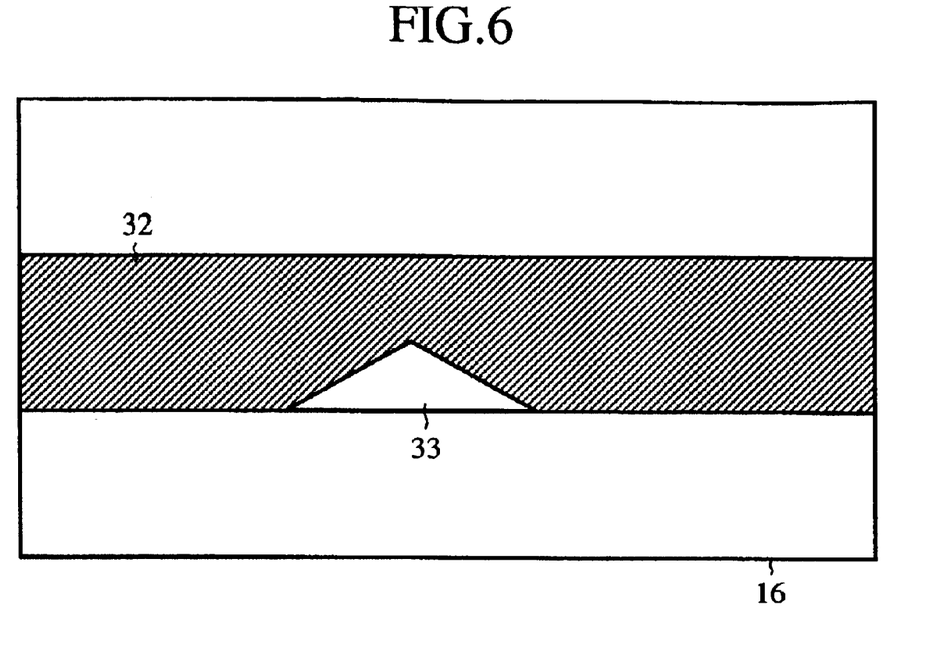
FIG. 6 is a view showing an example of an image taken by a photoelectric conversion device shown in FIG. 5.

Incidentally, the operation unit 14 may be displayed the wafer defect image on a monitor 16. That is, in the case where the operation unit 14 finds the anomalous detection angle information, when wafer 1 is rotated from the anomalous detection angle information by an angle designated by the positional relationship between the scattered light receiving part 13 and the photoelectric conversion device 31, an image given from the photoelectric conversion device 31 is displayed, as shown in FIG. 6, on the monitor 16 as the wafer defect image corresponding to the anomalous detection angle information (in FIG. 6, a reference numeral 32 denotes the end surface of the wafer 1 and a reference numeral 33 the defect (chip) on the wafer. In this manner, the operator can immediately identify the defect on the wafer 1 by the image.

Further, as shown by an ID 6 in FIG. 4, a check mark may be put in a column of an orientation flat (OF). That is, even if the wafer has no defect such as a flaw, if the image obtained from the photoelectric conversion device 31 has an orientation flat, for example, it may be manually put in the column a check mark implying the presence of the orientation flat on the wafer (wafer indicated by the ID 6 in FIG. 4) and filled its length (2 mm in FIG. 4).

As described above, according to the third embodiment, the wafer anomalous detection angle information and the intensity of detected scattered light at that time are stored together with the wafer processing information, so that it is possible to check the defect on the wafer in detail in the future.

Further, since the defect on the wafer (wafer defect image) can be obtained in correspondence with the wafer anomalous angle information, it is possible for the operator to correctly identify how the defect is.

Still further, it is possible to check the history of an anomalous wafer for each vendor and production line with reference to the wafer defect information file.

Fourth Embodiment

Figure 7:
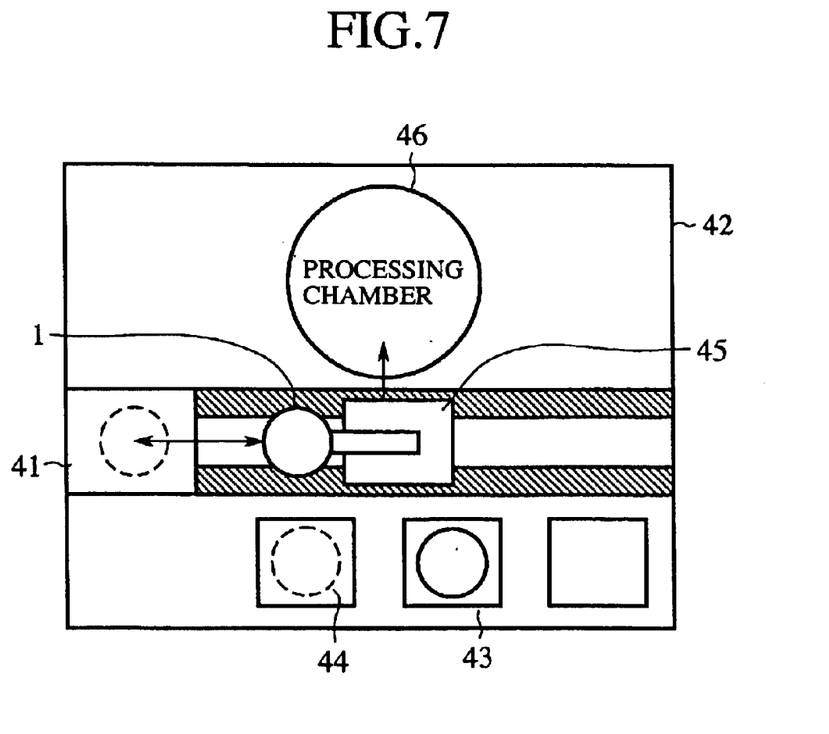
FIG. 7 is a block diagram showing a semiconductor production equipment according to a fourth embodiment of the present invention.

In FIG. 7, a reference numeral 41 denotes a defect inspecting device shown in FIG. 1 or FIG. 5, which is built in a semiconductor production equipment 42. The semiconductor production equipment 42 is mounted with a wafer loading cassette 43 and an anomalous (defective) wafer storage cassette 44 and many wafers are stored in the wafer loading cassette 43. Further, the semiconductor production equipment 42 is provided with a carrier robot 45 and a processing unit (processing chamber) 46 and, as will be described later, a wafer 1 is loaded to the defect inspecting device 41 from the wafer loading cassette 43 by the carrier robot 45. Then, as described above, after the positioning and the defect inspection of the wafer 1 are performed, if the defect inspection proved to be defect free, the wafer 1 is transferred to the processing chamber 46 by the carrier robot 45. Here, the carrier robot 45 is controlled by a main control unit (not shown).

Next, the operation of the defect inspecting device of the fourth embodiment will be described.

Under the control of the main control unit, the carrier robot 45 transfers the wafer 1 to the defect inspecting device 41 from the wafer loading cassette 43. The defect inspecting device 41, as described in FIG. 1 or FIG. 6, performs the positioning of the wafer 1 and the defect inspection (anomalous detection) on the wafer 1. Then, the defect inspecting device 41 sends an inspection signal indicative of whether or not there is any abnormality on the wafer 1 to the main control unit. If the inspection signal indicates that there is no abnormality on the wafer 1, the main control unit transfers the wafer 1 to the processing chamber 46 from the defect inspecting device 41 by the carrier robot 45. Then, the wafer 1 is subjected to a predetermined processing in the processing chamber 46 and finished the processing of the wafer. After the processing of the wafer 1 is finished, the main control unit controls the carrier robot 45 to transfer the processed wafer 1 from the processing chamber 46 to the wafer loading cassette 43 by the carrier robot 45 to load the processed wafer to the wafer loading cassette 43 again.

On the other hand, if the inspection signal indicates that there is an abnormality on the wafer 1, the main control unit transfers the wafer 1 to the anomalous wafer storage cassette 44 from the defect inspecting device 41 by the carrier robot 45 and the wafer 1 is stored in the anomalous wafer storage cassette 44. At this time, as described above, the wafer defect information file is created.

As described above, according to the fourth embodiment, the wafer judged to have an abnormality by the defect inspecting device is automatically stored in the anomalous wafer storage cassette and at the same time the wafer defect information file is created, so that it is possible to preclude the anomalous wafer from being sent to the processing chamber, thus preventing a trouble. Further, it is possible to check the defect in correspondence with the wafer defect information file stored in the anomalous wafer storage cassette.

EFFECTS OF THE INVENTION

As described above, according to the present invention, the substrate to be processed (wafer) is positioned and then is inspected while rotating it at least one rotation from the position where it is positioned, and if a defect is detected on the substrate, the defective position is determined as angle information indicative of the angle of rotation of the substrate and, therefore, the defective position on the substrate can be obtained as angle information. As a result, it is possible to detect the defective position on the wafer with high accuracy and easily when the substrate is positioned. This quickly addresses the defect and thus improves the productivity of the semiconductor device in producing a semiconductor device.

According to the present invention, the coordinate system defined by the angle of rotation and the intensity of the scattered light is displayed on the monitor, and the intensity of the scattered light and the threshold are displayed on the coordinate system depending on the angle of rotation of the substrate to be processed. Therefore, it is possible for the operator to see at a glance the intensity of scattered light over the threshold and where the defect is on the substrate.

According to the present invention, if a defect is detected on the substrate to be processed, an alarm signal is sent to an operator. Therefore, it is possible to attract the attention of the operator.

According to the present invention, the angle information is stored as an anomalous detection angle information in correspondence with the substrate to be processed. Therefore, it is possible to check in detail the abnormality on the substrate in the future.

According to the present invention, a substrate pattern representing the substrate to be processed is displayed based on the substrate information indicative of the dimension of the substrate and the defective position is displayed on the substrate pattern depending on the angle information. Therefore, it is possible to identify the defective position on the substrate with high accuracy.

According to the present invention, the anomalous image is obtained by taking the image of the defect on the substrate to be processed and the anomalous image is displayed on the monitor in correspondence with the angle information. Therefore, it is possible to observe the defect in detail by the anomalous image. At this time, if the angle information and the anomalous image are stored in the storage device in correspondence with the substrate, it is possible to check the abnormality on the substrate in detail and with high accuracy in the future.

What is claimed is:

1. A defect inspecting device for inspecting a substrate for defects, the defect inspecting device built in a positioning device configured for aligning the substrate for a subsequent semiconductor manufacturing process, the defect inspecting device comprising:

inspection means for inspecting the substrate for defects while rotating the substrate at least one rotation from a position where the substrate is aligned by the positioning device; and angle information calculating means for finding a defective position, when a defect is detected on the substrate, as angle information indicative of an angle of rotation of the substrate, the angle information determined based on the position where the substrate is aligned by the positioning device.

2. The defect inspecting device according to claim 1, wherein the inspection means comprises:

irradiating means for irradiating the substrate, light receiving means for receiving diffraction scattered light on the substrate as scattered light, and judging means for judging that a defect is detected on the substrate when the intensity of the scattered light exceeds a predetermined threshold.

3. The defect inspecting device according to claim 2, wherein the inspection means displays a coordinate system defined by the angle of rotation and the intensity of the scattered light on a monitor, and displays the intensity of the scattered light and the threshold on the coordinate system according to the angle of rotation of the substrate.

4. The defect inspecting device according to claim 2, wherein the judging means sends an alarm signal when a defect is detected on the substrate.

5. The defect inspecting device according to claim 1, wherein the angle information calculating means comprises a storage device for storing the angle information as anomalous detection angle information.

6. The defect inspecting device according to claim 1, wherein the angle information calculating means is given substrate information indicative of the dimension of the substrate and displays a substrate pattern representative of the substrate based on the substrate information and the defective position on the substrate pattern based on the angle information.

7. The defect inspecting device according to claim 1, further comprising imaging means for obtaining an image of the defect on the substrate, wherein the angle information calculating means displays the image on a monitor according to the angle information.

8. The defect inspecting device according to claim 7, wherein the angle information calculating means comprises a storage device for storing the angle information and the image of the defect.

9. A method of manufacturing a semiconductor device, comprising the steps of:

placing a substrate in a positioning device where the substrate is aligned for a subsequent semiconductor manufacturing process;

inspecting a defect on the substrate to determine whether the substrate is a defect, while rotating the substrate at least one rotation from the position where the substrate is aligned by the positioning device; and finding a defective position, when a defect is detected on the substrate, as angle information indicative of an angle of rotation of the substrate, the angle information determined based on the position where the substrate is aligned by the positioning device.

10. The method of manufacturing a semiconductor device according to claim 9, further comprising the steps of:

sending an alarm signal when it is determined that the substrate has a defect; and raising an alarm upon reception of the alarm signal to temporarily stop a semiconductor manufacturing process.

11. The method of manufacturing a semiconductor device according to claim 9, further comprising the step of suspending the semiconductor manufacturing process to be made to the substrate when it is determined that the substrate has a defect.

* * * * *